(12) United States Patent
Sameh

(10) Patent No.: US 7,702,523 B2
(45) Date of Patent: Apr. 20, 2010

(54) WEBSITE MESSAGING SYSTEM

(76) Inventor: Joseph Sameh, 2722 Old Glenview Rd., Wilmette, IL (US) 60091

( * ) Notice: Subject to any disclaimer, the term of this patent is extended or adjusted under 35 U.S.C. 154(b) by 2444 days.

(21) Appl. No.: 10/115,393

(22) Filed: Apr. 3, 2002

(65) Prior Publication Data

US 2003/0191663 A1   Oct. 9, 2003

(51) Int. Cl.
*G06Q 10/00*   (2006.01)
(52) U.S. Cl. .............................. 705/2; 705/3; 600/300
(58) Field of Classification Search .............. 705/2, 705/3; 600/300
See application file for complete search history.

(56) References Cited

U.S. PATENT DOCUMENTS

| | | | |
|---|---|---|---|
| 5,619,991 A | | 4/1997 | Sloane |
| 5,911,687 A | | 6/1999 | Sato et al. |
| 5,982,863 A | | 11/1999 | Smiley et al. |
| 6,004,276 A | * | 12/1999 | Wright et al. ............... 600/508 |
| 6,018,713 A | * | 1/2000 | Coli et al. ....................... 705/2 |
| 6,021,190 A | * | 2/2000 | Fuller et al. ............ 379/212.01 |
| 6,147,977 A | | 11/2000 | Thro et al. |
| 6,188,673 B1 | * | 2/2001 | Bauer et al. ................. 370/252 |
| 6,208,974 B1 | | 3/2001 | Campbell et al. |
| 6,314,405 B1 | | 11/2001 | Richardson |
| 6,345,260 B1 | * | 2/2002 | Cummings et al. ............. 705/8 |
| 6,385,589 B1 | * | 5/2002 | Trusheim et al. ............... 705/2 |
| 6,757,898 B1 | * | 6/2004 | Ilsen et al. ................... 709/203 |
| 7,024,462 B1 | * | 4/2006 | McErlean ................... 709/207 |
| 2002/0165732 A1 | * | 11/2002 | Ezzeddine et al. ............. 705/2 |
| 2002/0178030 A1 | * | 11/2002 | Loeb .............................. 705/2 |
| 2003/0028399 A1 | * | 2/2003 | Davis et al. ..................... 705/2 |
| 2004/0006490 A1 | * | 1/2004 | Gingrich et al. ................ 705/2 |

FOREIGN PATENT DOCUMENTS

WO   WO 01/29688   4/2001

OTHER PUBLICATIONS

Health Management Technology, v21, 1, p. 28, Jan. 2000. See article on Healinx Corp.*
TeleVox "Doctor Patient Communication".
WebMD "About Us".

* cited by examiner

*Primary Examiner*—C. Luke Gilligan
*Assistant Examiner*—Martin A Gottschalk

(57) ABSTRACT

A method and apparatus are provided for processing a message from a patient for one of a plurality of physicians through a web site. The method includes the steps of providing one or more web pages to the patient from the web site containing indicia of identity for each physician of the plurality of physicians and detecting selection by the patient of a physician of the plurality of physicians. The method further includes the steps of determining an information content of the message and routing the message based upon the determined information content and a predetermined routing criteria provided by the selected physician.

35 Claims, 6 Drawing Sheets

FIG. 3

Dr. John Jones

ARE YOU A?

- 152 — ☐ EXISTING PATIENT
- 154 — ☐ NEW PATIENT
- 156 — ☐ PHARMACIST
- 158 — ☐ MEDICAL SUPPORT STAFF
- 160 — ☐ OTHER

FIG. 4

EXISTING PATIENT OF DR. JONES

ARE YOU?

- ☐ RETURNING THE DOCTOR'S CALL (172)
- ☐ CALLING A SECOND TIME (174)
- ☐ CANCELLING TOMORROW'S SURGERY (176)
- ☐ REQUESTING LAB RESULTS (178)
- ☐ PATIENT OUT OF TOWN AND NEED A PRESCRIPTION (180)
- ☐ A NEW PATIENT WITH APPOINTMENT NEEDS TO TALK (181)

DO YOU?

- ☐ HAVE AN EMERGENCY (182)
- ☐ HAVE A PROBLEM WITH MEDICATION (186)
- ☐ HAVE A QUESTION ABOUT TOMORROW'S SURGERY (190)
- ☐ HAVE PAIN
- ☐ HAVE A MEDICAL QUESTION (184)
- ☐ HAVE A BILLING QUESTION (188)
- ☐ IF YOU HAVE A FEVER, ENTER YOUR TEMPERATURE (192)

[SUBMIT]

IS THIS REQUEST FOR

- ☐ YOURSELF (194)
- ☐ SPOUSE (196)
- ☐ DEPENDENT (198)

WHAT IS YOUR NAME? 200

HOW MAY I CONTACT YOU? 202

PLEASE DESCRIBE THE PROBLEM 204

FIG. 5

NEW PATIENT FOR DR. JONES

ENTER NAME ⟶ 212

ADDRESS ⟶ 214

TELEPHONE NUMBER ⟶ 216

WHEN DO YOU WANT TO SEE DR. JONES
- 218 ☐ IMMEDIATELY
- 220 ☐ THIS WEEK
- 222 ☐ AS SOON AS POSSIBLE

224 ⟶ IDENTIFY INSURANCE CARRIER

228 ☐ REFERRAL FROM DR. ⟶ 229

SUBMIT

DESCRIBE YOUR SYMPTOMS ⟶ 226

FIG. 6

PHARMACIST

IS THIS ABOUT?
- ☐ A NEW PRESCRIPTION — 232
- ☐ REFILL REQUEST — 234
- ☐ PHARMACY QUESTION — 236

YOUR NAME ⟶ 238

HOW MAY I CONTACT YOU ⟶ 240

PATIENTS NAME ⟶ 242

SUBMIT

PLEASE SUMMARIZE ⟶ 244

FIG. 7

MEDICAL STAFF MESSAGE

ARE YOU?

☐ OTHER DOCTOR   ☐ A HOSPITAL   ☐ PROVIDING NORMAL LAB RESULTS   ☐ PROVIDING CRITICAL LAB RESULTS

IS THIS ABOUT?

☐ ADMISSIONS/ TRANSFERS   ☐ CONSULTS   ☐ NURSING HOME/ HOSPICE   ☐ ORDERS

☐ PATIENT EXPIRATION NOTICE   ☐ DEATH CERTIFICATE (FUNERAL HOME/CORONER)

YOUR NAME

HOW MAY I CONTACT YOU

PATIENTS NAME

[ SUBMIT ]

PLEASE SUMMARIZE

KEY WORDS
TYPE: XXX - - - XXX ← 292
SUBTYPE: XXX - - - XXX ← 294

296

ROUTING ENTRY FORM

ENTER PIN — 302　　　ENTER NAME — 304

ROUTE TO:
ENTER DESTINATION AND RELATIVE ORDER

TELEPHONE | ORDER | PRIORITY
306　308　322

PAGE | ORDER | PRIORITY
310　312　324

E-MAIL | ORDER | PRIORITY
314　316　326

ROUTE TO ON-CALL DOCTOR
FROM　TO　BETWEEN AM　PM
318　320

ROUTE TO
322

WEBSITE MESSAGING SYSTEM

FIELD OF THE INVENTION

The field of the invention relates to physician/patient contact and more particularly to methods of forwarding messages from a patient to a physician.

BACKGROUND OF THE INVENTION

Good communication between doctor and patient has always been an important part of healthcare. While face-to-face communication has always been the best form of communication, it is also often necessary for physicians to remain available after hours for emergencies and other patient concerns.

The traditional method of contacting a physician after hours has been through an answering service. Answering services answer calls directed to the physician and take messages. The physician may periodically call the answering service to pick up his messages. Alternatively, the answering service may page the physician for each message, if the physician has a pager.

While answering services work well for taking and retrieving messages, some calls could be handled without the physician's involvement. However, only the physician is qualified to make a decision regarding the handling of his patients by others.

Because of the variability of patient handling procedures among medical specialties, conventional systems are often not structured to incorporate the needs of the individual physician and his practice. Accordingly, a need exists for a method of processing patient calls that can be structured to meet a variety of patient needs.

SUMMARY

A method and apparatus are provided for processing a message from a patient for one of a plurality of physicians through a web site. The method includes the steps of providing one or more web pages to the patient from the web site containing indicia of identity for each physician of the plurality of physicians and detecting selection by the patient of a physician of the plurality of physicians. The method further includes the steps of determining an information content of the message and routing the message based upon the determined information content and a predetermined routing criteria provided by the selected physician.

BRIEF DESCRIPTION OF THE DRAWINGS

FIG. 3 is a classification screen that may be used by the system of FIG. 1;

FIG. 4 is an existing patient screen that may be used by the system of FIG. 1;

FIG. 5 is a new patient screen that may be used by the system of FIG. 1;

FIG. 6 is a pharmacist screen that may be used by the system of FIG. 1;

FIG. 7 is a medical staff screen that may be used by the system of FIG. 1;

DETAILED DESCRIPTION OF AN ILLUSTRATED EMBODIMENT

Figure 1:
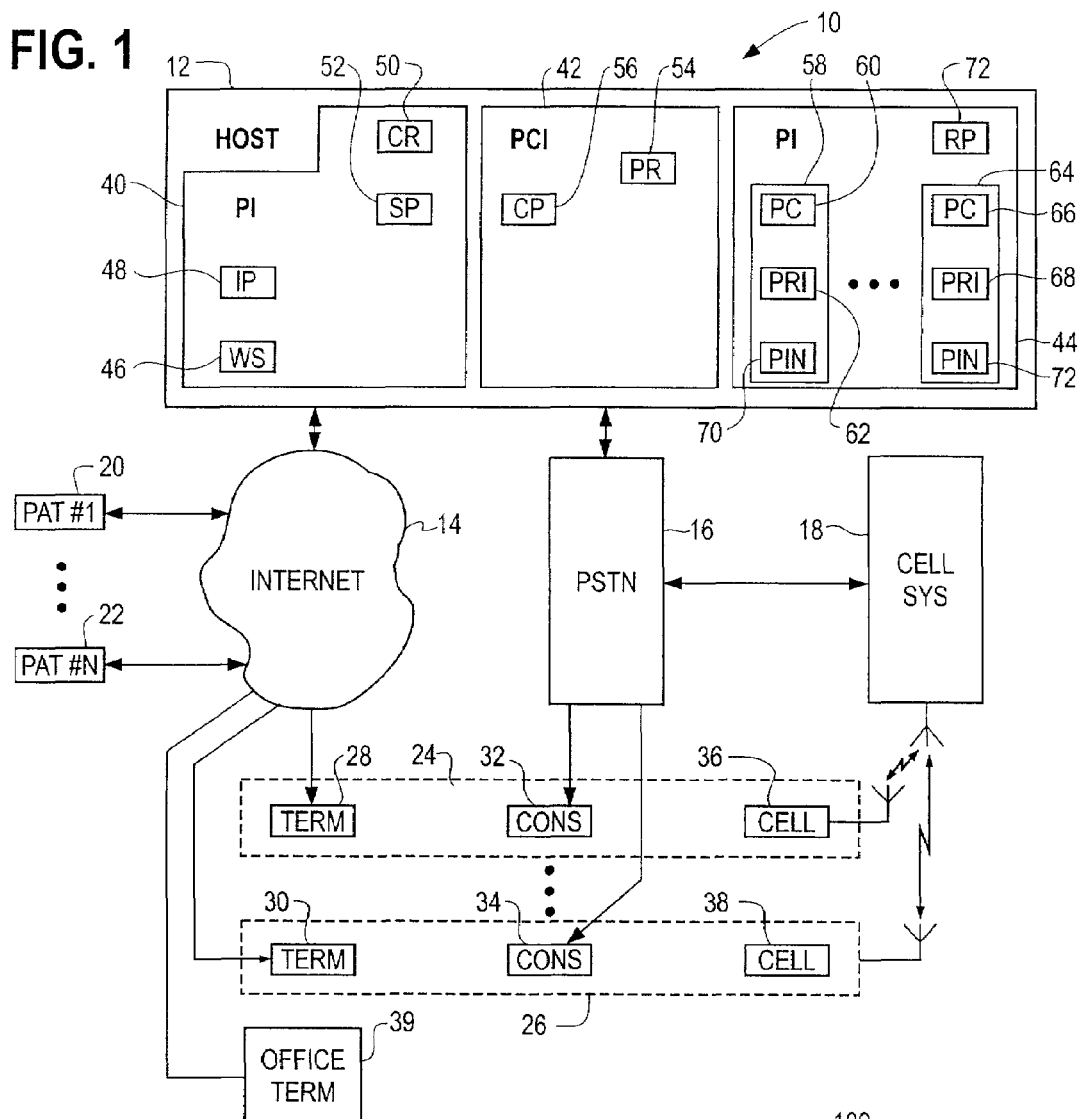
FIG. 1 is a block diagram of a website messaging system under an illustrated embodiment of the invention.

FIG. 1 is a block diagram of a website messaging system 10 shown generally in accordance with an illustrated embodiment of the invention. The website messaging system 10 may be used to forward messages from patients to their attending physicians under any of a number of predetermined message formats and patient conditions specified by the attending physician.

The system 10 may also be used by associates of the physician (e.g., labs, pharmacies, etc.) to forward messages about patients to the attending physician. Because of the flexibility of the system 10 in handling messages the term "patient" or "requestor" is often used herein generically to refer to any of patients, associates of the physician or to other physicians passing messages through the system 10.

The system 10 may include a number of different interfaces 40, 42, 44. A first interface 40 may function as a patient interface that is able to provide information to and receive information from a patient 20, 22. One of the primary functions of the patient interface 40 is to identify a patient's attending physician and to function as an interface between the patient and the identified attending physician from among the many other physicians that may also use the system 10.

A second interface 42 may function as a processing center interface. The processing center interface 42 may function to receive information from the patient 20, 22 and determine a priority of the message.

A third interface 44 may function as the physician interface 44. The physician interface 44 functions to deliver the messages based upon the determined nature of the request and a set of delivery instructions provided by the physician.

The physician interface 44 may include a number of physician's records 58, 64, including one record for each physician using the system 10. Each record 58, 64 may include a physician's priority criteria 62, 68 and also a set of physician's routing instructions 62, 68 for routing requests to the physician.

The physician interface 44 may function to deliver messages to physicians under any of a number of communication formats (e.g., Internet, voice channel through the public switched telephone network (PSTN), voice channel through a cellular system, data through a cellular system, pager, palm pilot etc.). Because of the multiplicity of communication channels through which a request may be delivered, a communication sphere 24, 26 may be defined for each physician.

The communication sphere 24, 26 may be defined in a metaphysical sense as the physical space proximate the physician that may contain one or more communication devices. For example, if a first physician and his associated communication sphere 24 (the physician and communication sphere sometimes referred to hereinafter, together, as the "physician 24") were located in his office (either in his home or in his clinic), then he may have access to a computer terminal 28, a telephone console 32 and a cell phone 36, all at the same time. In this case, the communication sphere 24 of the first physician may include the computer terminal 28, the telephone console 32 and the cell phone 36, as shown in FIG. 1.

If the physician 24 should leave his office and take his cell phone 36 with him, then the physician's communication sphere 24 would only include the cell phone 36. Further, if the first physician 24 should leave his office and enter the office of a second physician 26, then the communication sphere 24 of the first physician may also include the communication devices 30, 34, 38 that are also within the communication sphere 26 of the second physician.

In order to accommodate the mobile nature of physicians, the physician interface 44 may be easily altered to include the changing range of communication devices located within the communication sphere 24, 26 of the physician. It should also be noted that the physician interface 44 may be altered to include the communication devices subscribed to by the physician or the communication devices of other physicians or non-physicians. In addition, while only two communication sphere 24, 26 are shown in FIG. 1, any number of spheres 24, 26 and any number of communication devices 28, 30, 32, 34, 36, 38 may be accommodated by the system 10.

Turning first to the patent interface 40, an explanation will first be offered of the interface 40 and how it functions to collect relevant information. Following a description of the patient interface 40, an explanation will be provided of the processing center interface 42 and of the physician interface 44.

In order to facilitate the simple and convenient use of the patient interface 40, the interface 40 may allow a patient 20, 22 to contact his physician through a web site (e.g., with a URL of "NeedMyDoctor.com"). Contacts through the web site 46 may be routine (e.g., making an appointment, obtaining a renewal of a prescription, etc.) or on a more urgent basis (e.g., an emergency).

Identification of a patient's physician may be accomplished automatically in the case of an existing patient by storing an identifier of the attending physician as a cookie in a browser of a computer terminal 20, 22 of the patient. In the alternative, new patients may be offered the opportunity to select a physician based upon the needs and preferences of the patient 20, 22.

Upon accessing the web site 46, an identity processor 48 may attempt to identify the patient 20, 22. Identification of the patient 20, 22 may be accomplished by retrieving a URL of the party accessing the web site 46 or by retrieval of any cookies present within the browser of the accessing party 20, 22. In either case, the URL or cookies may be compared with the contents of a set of customer records 50 to identity any physicians that the patient 20, 22 may have previously selected.

Figure 2:
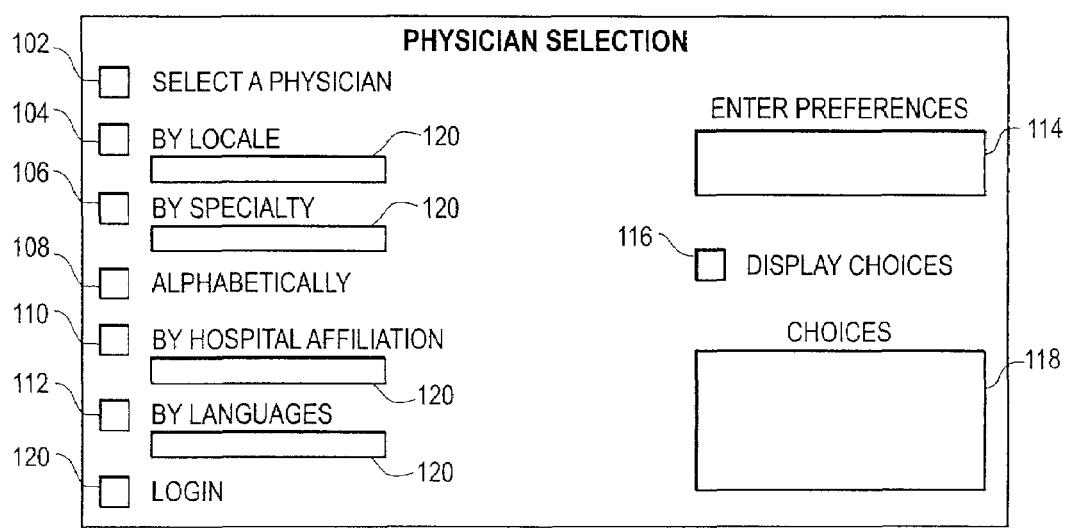
FIG. 2 is a physician selection screen that may be used by the system of FIG. 1.

In either case, a screen (web page) 100 (FIG. 2) may be downloaded to a browser of the patient or other requester 20, 22. If the patient 20, 22 has previously used the system 10 and has previously selected a physician, then any selected physicians may be displayed within a CHOICES box 118.

If the patient 20, 22 has previously used only a single physician, then a name, image and biography of the physician may be displayed in the choice box 118. The patient 20, 22 may select this physician by activating a SELECT A PHYSICIAN button (softkey) 102 or by activation of an ENTER button on his terminal 20, 22.

If the patient 20, 22 has previously used or selected more than one physician, then a list of the names of previously selected physicians may be displayed in the CHOICES box 118. The patient 20, 22 may either select a physician from among those displayed in the CHOICES box 118 or select yet another physician by activation of one or more criteria selection boxes 104, 106, 108, 110, 112. If the patient 20, 22 selects from among the list of previously selected physicians within the box 118, then a name and image of the physician may be displayed and the patient 20, 22 may be proceed as described above.

If the patient 20, 22 chooses to select another physician, then he may select the other physician based upon any of a number of different criteria (e.g., locale, medical specialty, hospital affiliation, language ability, etc.). Further, the patient 20, 22 may refine his search by using a preferences window 114.

For example, the patient 20, 22 may enter an "A" in the preferences window 114 and activate a LOCALE button 120. Alternatively, the patient 20, 22 may activate the LOCALE button 104, enter an "A" in the box 114 and select the DISPLAY CHOICES button 116. In response, a selection processor 52 within the patient interface 40 may provide the patient with a set of choices on locale that begin with "A" (e.g.: Alabama; Alaska; Albany, N.Y. etc.).

The patient 20, 22 may make a selection and proceed to another search criteria. Upon making a selection, the selection may appear in a criteria display 120 associated with the criteria.

If the patient 20, 22 should then activate the BY HOSPITAL AFFILIATION button 110, then a list of hospitals in the selected locale may be displayed in the CHOICES box 118. As above, the patient 20, 22 may make a selection and the selection may appear in the box 120 associated with the selected criteria.

The patient 20, 22 may then select a specialty and, possibly a language preference. The patient 20, 22 may then select an ALPHABETICALLY button 108 to view a list of physicians under the combination of criteria chosen. The patient 20, 22 may select a physician from the list shown in the CHOICES area 118 and activate the SELECT A PHYSICIAN button 102 to complete the process.

As a much simpler alternative, the patient may simply enter a physician's name in the ENTER PREFERENCES box 113 and activate the SELECT A PHYSICIAN box 102. The name and image of the physician may appear in the CHOICES box 118. The patient 20, 22 may then review his choice and then activate the SELECT A PHYSICIAN box 102 a second time to complete selection of the physician.

The ability to enter a physician's name is a tremendous advantage for people who are traveling and experience a medical problem. In this case, the requester 20, 22 may simply go to any computer and access the website 46 remotely.

Following selection of a physician, the web page 150 (FIG. 3) may be downloaded to the patient 20, 22. Included within the web page 150 may be a number of classification buttons 152, 154, 156, 158, 160 for each message. While any method of classification may be used one method divides the messages according to whether the source is an existing patient, a new patient, medical support staff or other. Activation of an EXISTING PATIENT button 152 may be used to indicate that the patient 20, 22 is already under the care of the physician. Activation of an NEW PATIENT button 154 may be used to indicate that the patient 20, 22 has never seen the physician. Activation of the PHARMACIST button 156 may be used to indicate that the requester 20, 22 may be a pharmacist with a question about a prescription. Activation of the MEDICAL SUPPORT STAFF button 158 may indicate a message from another physician or a message from a person providing support services to the physician. Finally, activation of the OTHER button 158 may be used for any other purpose selected by the physician.

If the patient 20, 22 should activate the EXISTING PATIENT button 152, then the screen 170 of FIG. 4 may be downloaded to the patient 20, 22. Within the screen 170, a first set of boxes (softkeys) 172, 174, 176, 178, 180, 181 may be provided for entering an overall reason for the message. A second set of boxes 182, 184, 186, 188, 190, 192 may be provided for determining a physical state of the patient. A text entry window 192 may be provided for entry of a patient temperature.

Another text box 200 may be provided for entry of a name of the requestor 20, 22. A text box 202 may also be provided for entry of a communication path (e.g., telephone number, e-mail address, pager number, etc.) through which the physician can reach the requester 20, 22. The requester 20, 22 may also be able to identify through a set of softkeys 194, 196, 198 whether the requester is the patient or whether the patient is a relative. A text box 182 may be provided for entry of a description of the problem.

If the patient 20, 22 should activate the NEW PATIENT softkey 154, then a screen 210 of FIG. 5 may be downloaded to the requester 20, 22. Text boxes 212, 214, 216 may be provided for entry of a name, address and contact information of the patient. A softkey 228 and textbox 229 combination may be used to identify the patient as a referral and the source of the referral. Selection buttons 218, 220, 222 may be provided for scheduling an appointment. A text box 224 may be provided for entry of insurance information. Finally, a large text box 226 may be provided for entry of descriptive information regarding the reason for the appointment.

If the requester 20, 22 should activate the PHARMACIST softkey 156 on FIG. 3, then the screen 230 of FIG. 6 may be downloaded to the requester 20, 22. Within the screen 230, the requester 20, 22 may be provided with text boxes 238, 240 for identification of the requester and to enter contact information. A set of softkey boxes 232, 234, 236 may be provided for the requester to differentiate between questions about new prescriptions, refills and general pharmacy questions.

If the requester 20, 22 should activate the MEDICAL SUPPORT STAFF button 158, then the screen 250 of FIG. 7 may be downloaded to the requester 20, 22. Within the screen 250, the requester 20, 22 may be asked to enter his name and contact information in one set of boxes 272, 274. Another set of boxes 252, 254, 256, 258, 260, 262, 264, 266, 268, 279 may be provided for entry of a context of the request.

In addition, a text box 276 may be provided for entry of a patient's name. Another text box 278 may be provided for entry of a message regarding the patient. A SUBMIT button 280 allows the requester 20, 22 to return the message to the system 10.

If the requester 20, 22 should activate the OTHER box 158, then a single blank text box may be downloaded. The OTHER button 158 may be used for any of a number of purposes as described in more detail below.

Upon completion of selection of a physician and of the entry of information through the text boxes of FIGS. 3-7, the message may be transferred to the processing center interface 42. Within the processing center interface 42, a content processor 56 may process each message to determine a nature and content of the request based upon the information elements provided through the web pages (e.g., the identity of the requester, any classification information provided through the classification buttons and any text information received through the text boxes).

Based upon the determined nature and content of the request, a relative importance may be assigned to the request, based upon a subjective criteria provided by the physician. The criteria is necessarily subjective because the relative importance of information elements varies from one physician's practice to another physician's practice and in accordance with the preferences of one physician over another physician.

For example, physicians with a practice limited to surgery may only classify messages from hospitals or other surgeons or patients with post operative problems as significant enough to justify an expedited message to the physician. Other messages to the surgeon may be regarded as much less important.

In the alternative, a physician with a practice limited to pediatric care may only consider children with high fevers, broken bones or severe bleeding as important. Other requests related to less severe trauma may be considered to be less important. Further the criteria for routing messages to a physician may be changed based upon the time of day.

For example, during normal office hours, all messages may be routed to a nurse or other assistant at a clinic or hospital where the physician is normally to be found during those hours. After normal office hours, messages may be routed to the physician only when the physician is on call. When the physician is not on call, any requests to the physician may be automatically routed to another designated physician.

Figure 8:
FIG. 8 is a priority selection screen that may be used by the system of FIG. 1.

Based upon the nature of the request, the content processor 56 may route the message, by comparing an information content with a set of threshold values provided by the physician. FIG. 8 provides a screen 280 that may be downloaded to a terminal 28, 30 of a physician 24, 26 for purposes of setting threshold values for forwarding messages. The screen 280 may be downloaded to a physician during initial registration with the system 10 or at any time thereafter to change the routing format.

The screen 280 of FIG. 8 may be used by the physician to establish a multi-level message forwarding methodology. Under one embodiment, the box shown along the left side of each subject matter listing in screen 280 may be a text box where a number value indicating priority may be explicitly entered. For purposes of simplicity, the system 10 will be described as being based upon a two-level system of priorities. However, any number of priority levels could be used.

Also, for purposes of simplicity, the use of the screen 280 will be described using a system of default levels. Instead of entering a number in the box, the boxes may be used as softkeys. If the softkey is activated by the physician, then the subject matter of that softkey will be given the highest priority. If the softkey is not activated, then the subject matter will be given the second, lower level of priority.

At a highest, first level of importance, messages may be routed directly to a physician's sphere 24, 26. At the second level, requests may be routed to a secondary destination (e.g., an office of the physician).

For example, checking the box in the upper left corner (labeled "New prescription calls") would result in all messages from pharmacists about new prescriptions being given the highest priority and routed directly to the physician. Further, checking the box in the bottom of the right-side (labeled "Patient never seen has appt. and need to talk") would result in messages from first time patients begin routed on the first level.

In general, the solicitation and processing of messages from requesters 20, 22 within the content processor 56 may be controlled by a physician's criteria obtained by the system 10 through screen 280 and stored in a file 60, 66 for each physician. Once a physician 24, 26 has identified a routing criteria (e.g., using screen 280), the content processor 56 may retrieve the routing criteria for that physician 24, 26 and use the criteria for message routing.

As each webpage 150, 170, 200 is completed and returned to the system 10, the content processor 56 may examine the content of the webpage 150, 170, 200 under the criteria provided by the associated physician 24, 26. A determination of the nature and importance of the message may occur on any of a number of different levels.

On a first level, the processor 56 may determine the type of message based upon the information elements provided through screens 170, 210, 230, 250. Following a determination of the type of message, the content processor 56 may perform an element-by-element comparison between selected items for that message type on screen 280 and the content of the message.

The message type of STANDARD HOLD FOR OFFICE CALLS would always be classified as a low priority unless the physician indicated otherwise. If the physician has selected "Appointments", then messages from new patients where the softkey 154 is activated would be given a high priority. The selections for "Billing questions" and "Prescription exceptions" may be given similar treatments.

Messages from patients may be processed somewhat differently. For example, a physician may not only select the option "Fever over _____", but may also specify a priority limit for the fever. Detection may be accomplished by a comparison of the numeric value entered through the text box 192 and the threshold value provided by the physician. Alternatively, the physician may specify any fever within one week post operatively.

On another level, the physician 24, 24 may also set a criteria for message routing based upon key word searching using words entered through any of the text boxes 202, 204, 226, 238, 242, 244, 272, 272, 276, 278. For example, the physician 24, 26 may go to screen 280 of FIG. 8 and double click on any element or sub-element to bring up a text box associated with that element. For example, the physician 24, 26 may double click on the "OTHER" category on screen 280. In response, the text box 290 of FIG. 9 may be downloaded to the physician's terminal 28, 30. Within the text box 290, a first line 292 may indicate the type of text box as being "OTHER". Since the "OTHER" category does not have a sub-element, the second line 294 may be blank.

Upon entering the text box 290, the physician 24, 26 may enter his wife's name (e.g., "Jane Jones") or some other word identifying his wife. Entry of his wife's name as a criteria for the "OTHER" category allows any message sent under the "OTHER" classification and that includes his wife's name or identifier to be given a high routing priority.

To use the facility, the physician's wife would enter the web site 46, type her husband's name in text box 114 and activate "SELECT A PHYSICIAN". On the next downloaded screen 150, the wife would select "OTHER". In response, a blind screen would appear within which the physician's wife may type "From: Jane Jones" and a message. Upon receiving the message, the content processor 56 would compare the key words "Jane Jones" with the content of the message and recognize the matching words "Jane Jones" present in the message header. Based upon the match, the content processor 56 would route the message at the highest priority level.

Alternatively, the physician may also click on "PATIENT-ORIGINATED CALLS" on screen 280 and enter a patient's name. Based on key word searching, any message from that patient would be routed at the highest priority.

The use of key word searching allows a physician to customize call routing for any time period (e.g., 2 hours, 2 days, permanently, etc.) to meet the needs of critically ill patients. Alternatively, if the physician is part of a surgical team waiting for a transplant donor, key word searching could be used to automatically identify messages from other members of the surgical team.

Once the content processor 56 determines an information content and priority level of a message, the content processor 56 may transfer the message to a routing processor 72 within the physician's interface 44. Within the physician's interface 44, the routing processor 72, may retrieve a set of routing instructions 68 based upon the priority level determined by the content processor 56.

Located within the routing instructions 68 may be a prioritized list of communication devices within the physician's communication sphere 24, 26. Messages may be routed to the physician 24, 26 based upon the entries within the prioritized list.

Figures 9, 10:
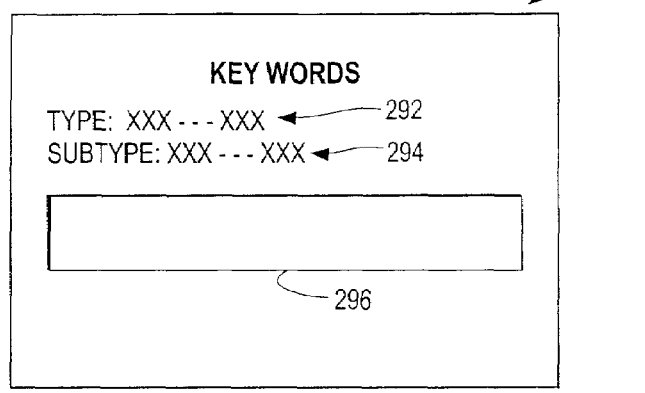
FIG. 9 is a key word entry screen that may be used by the system of FIG. 1.
FIG. 10 is a routing priority screen that may be used by the system of FIG. 1.

FIG. 10 depicts a routing webpage 300 that may be downloaded from the web site 46 to a terminal 28, 30 of the physician. The routing webpage 300 may be accessed by first accessing the physician identification webpage 100 (FIG. 1) and activating LOGIN softkey 120.

Within the webpage 300, the physician may first be required to enter his personal identifier number (PIN) into a first box 302. Upon entering his PIN number the terminal 28, 30 may upload the PIN to the routing processor 72 where the PIN is compared with the PINs 70, 72 of other physicians using the system 10.

If a match is found, the routing processor 72 may download a name of the physician to be displayed in a first box 304 and a current content of the physician routing instructions 62, 68 to be displayed in other boxes 306, 310, 314.

Included with each routing destination is an ordering number 308, 312, 316 and priority ranking 322, 324, 326. The ordering number indicates the relative position of the routing destination in the routing list for any particular priority level. For example, at the highest priority level, if the physician wishes to be paged first, then the pager number would appear at a top of a list in box 310 with a number "1" shown opposite the pager number in an order list 312 and a "1" in the priority ranking. If the physician wishes to simultaneously receive a hardcopy of the message on his computer 28, 30, then an e-mail address of his computer may appear on the top of list in an e-mail box 314 opposite another number "1" in the order box 316 and a "1" in the priority ranking. Once the physician downloads the screen 300, he may make new entries, delete old entries or change the order at will.

In addition to setting up a routing list, the physician 24, 26 may also set up a schedule when he/she is not to receive messages (i.e., the physician is not on call). As shown, the physician simply enters his dates and hours when the physician is not on call and when calls should be routed to another physician. The entry of time periods into boxes 318, 320 simply causes messages to be routed to an alternate physician in an on call list maintained within the system 10. An identifier of the alternate physician may be entered into a "ROUTE TO" text box 322.

Delivery of the messages may occur under any of a number of different formats. For example, if the physician's computer 28, 30 is the destination of a message, then the delivered message may have the same format as shown in FIGS. 2-7. Alternatively, the format of FIGS. 2-7 may be changed to delete unnecessary information.

If the destination is a cell phone or a telephone, then a voice synthesizer may be used to present the messages of FIGS. 2-7 under a predefined audio format. Alteration of the call list based upon screen 300 may also be accomplished using a telephone, the voice synthesizer and keypad selection on the telephone.

Once a message has been delivered to the physician 24, 26, the routing processor 72 may send a message back to the patient interface 40 and patient 20, 22 confirming receipt of a high priority message by the physician. Where the physician responds to the patient's message through the system 10, the routing processor 72 may also calculate an average time for the physician to respond. In such cases, the routing processor 72 may also include an estimate of the expected time for the physician to respond in the message to the patient 20, 22.

A specific embodiment of a method and apparatus for routing physician messages through a website has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention, any and all modifications, variations, or equivalents that fall within the true spirit and scope of the basic underlying principles disclosed and claimed herein.

The invention claimed is:

1. A method of routing a message from a requestor to a physician through a web site, such method comprising the steps of:
   the physician providing a plurality of message destinations;
   the physician providing a respective criteria for routing messages to each of the plurality of message destinations;
   the requestor accessing the web site and downloading a form;
   the requestor at least partially completing the form and returning the form to the web site as a message to the physician;
   determining an information content of the message received from the requestor;
   selecting a message destination of the plurality of destinations with the respective routing criteria that matches the determined message content; and
   routing the message to the selected message destination based upon the determined information content and routing criteria provided by the physician.

2. The method of processing the message as in claim 1 further comprising the web site providing one or more web pages containing a listing of a plurality of physicians based upon one or more of locale, medical specialty, hospital affiliation and language.

3. The method of processing the message as in claim 2 further comprising dividing the listing by alphabet.

4. The method of processing the message as in claim 2 further comprising selecting the physician from the plurality of physicians.

5. The method of processing the message as in claim 4 further comprising downloading a biography of the selected physician.

6. The method of processing the message as in claim 4 further comprising downloading an image of the selected physician.

7. The method of processing the message as in claim 1 wherein the step of routing the message further comprises comparing the determined information content with each of the plurality of routing criteria provided by the physician.

8. The method of processing the message as in claim 7 further comprising routing the message to the physician as a high priority message to a high priority message destination of the plurality of destinations when the determined information content of the request meets a high priority routing criteria of the plurality of routine criteria provided by the physician.

9. The method of processing the message as in claim 8 wherein the step of routing the message to the physician further comprises placing a telephone call to the physician at a telephone number specified by the physician when the determined information content of the request meets a routing criteria for the telephone number provided by the physician.

10. The method of processing the message as in claim 8 wherein the step of routing the message to the physician further comprises paging the physician at a telephone number specified by the physician when the determined information content of the request meets a routing criteria for paging provided by the physician.

11. The method of processing the message as in claim 8 wherein the step of routing the message to the physician further comprises sending the message as an e-mail to the physician at an e-mail address specified by the physician when the determined information content of the request meets a routing criteria for e-mails provided by the physician.

12. The method of processing the message as in claim 7 further comprising routing the message to an assistant of the physician as a lower priority message when the determined information content of the request does not meet the routing criteria provided by the physician.

13. The method of processing the message as in claim 1 further comprising downloading a criteria selection webpage to the physician.

14. The method of processing the message as in claim 1 further comprising sending a message to the patient confirming receipt of the message.

15. The method of processing the message as in claim 14 wherein the step of sending a confirming message further comprises including an estimate of a time period that will elapse before a response will be received by the patient based upon the routing of the message.

16. An apparatus for routing a message from a requestor to a physician through a web site, such apparatus comprising:
   means used by the physician for providing a plurality of message destinations;
   means used by the physician for providing a respective criteria for routing messages to each of the plurality of message destinations;
   means used by the requestor for accessing the web site and downloading a form;
   means used by the requestor for at least partially completing the downloaded form and returning the form to the web site as a message to the physician;
   means for determining an information content of the message received from the requestor;
   means for selecting a message destination of the plurality of destinations with the respective routing criteria that matches the determined information content; and
   means for routing the message to the selected message destination based upon the determined information content and routing criteria provided by the selected physician.

17. The apparatus for processing the message as in claim 16 wherein the web site further comprises means for providing one or more web pages containing a listing of a plurality of physicians based upon one or more of locale, medical specialty, hospital affiliation and language.

18. The apparatus for processing the message as in claim 17 further comprising means for dividing the listing by alphabet.

19. The apparatus for processing the message as in claim 17 further comprising means for selecting the physician from the plurality of physicians.

20. The apparatus for processing the message as in claim 17 further comprising means for downloading a biography of the selected physician.

21. The apparatus for processing the message as in claim 17 further comprising means for downloading an image of the selected physician.

22. The apparatus for processing the message as in claim 16 wherein the means for routing the message further comprises means for comparing the determined information content with each of the plurality of routing criteria provided by the physician.

23. The apparatus for processing the message as in claim 22 further comprising means for routing the message to the physician as a high priority message to a high priority message destination of the plurality of message destinations when the determined information content of the request meets a routing criteria of the high priority message destination provided by the physician.

24. The apparatus for processing the message as in claim 23 wherein the means for routing the message to the physician further comprises placing a telephone call to the physician at a telephone number specified by the physician when the determined information content of the request meets a routing criteria of the telephone call provided by the physician.

25. The apparatus for processing the message as in claim 24 wherein the means for routing the message to the physician further comprises means for paging the physician at a telephone number specified by the physician when the determined information content of the request meets a routing criteria for paging provided by the physician.

26. The apparatus for processing the message as in claim 25 wherein the means for routing the message to the physician further comprises means for sending the message as an e-mail to the physician at an e-mail address specified by the physician when the determined information content of the request meets a routing criteria for e-mail provided by the physician.

27. The apparatus for processing the message as in claim 22 further comprising means for routing the message to an assistant of the physician as a lower priority message when the determined information content of the request does not meet a predetermined criteria provided by the physician.

28. The apparatus for processing the message as in claim 16 further comprising means for downloading a criteria selection webpage to the physician.

29. The apparatus for processing the message as in claim 16 further comprising means for sending a message to the patient confirming receipt of the message.

30. The apparatus for processing the message as in claim 29 wherein the means for sending a confirming message further comprises means for including an estimate of a time period that will elapse before a response will be received by the patient based upon the routing of the message.

31. An apparatus for routing a message from a requestor to a physician through a web site, such apparatus comprising:
- a plurality of message destinations provided by the physician;
- a respective criteria provided by the physician for routing messages to each of the plurality of message destinations;
- a form downloaded by the requestor from the web site;
- an at least partially completed form created by the requestor from the downloaded form and returned to the web site as a message to the physician;
- a content processor adapted to determine an information content of the message received from the patient and that selects a message destination of the plurality of message destinations by matching the routing criteria of the selected destination with the determined information content; and
- a routing processor adapted to route the message to the selected message destination based upon the determined information content and routing criteria provided by the selected physician.

32. The apparatus for processing the message as in claim 31 wherein the web site further comprises one or more web pages containing a listing of a plurality of physicians based upon one or more of locale, medical specialty, hospital affiliation and language.

33. The method of processing the message as in claim 1 wherein the step of routing the message further comprises routing the call to another designated physician when the physician is not on call.

34. The apparatus for processing the message as in claim 16 wherein the means for routing the message further comprises means for routing the call to another designated physician when the physician is not on call.

35. The apparatus for processing the message as in claim 1 wherein a respective criteria of one of the plurality of message destinations further comprises the physician is not on call.

* * * * *